United States Patent
Terashima et al.

(10) Patent No.: US 12,133,725 B2
(45) Date of Patent: Nov. 5, 2024

(54) GAIT ANALYSIS APPARATUS, GAIT ANALYSIS METHOD, AND COMPUTER-READABLE RECORDING MEDIUM

(71) Applicant: NEC Solution Innovators, Ltd., Tokyo (JP)

(72) Inventors: Hiroki Terashima, Tokyo (JP); Katsuyuki Nagai, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 522 days.

(21) Appl. No.: 17/441,802

(22) PCT Filed: Feb. 12, 2020

(86) PCT No.: PCT/JP2020/005349
§ 371 (c)(1),
(2) Date: Sep. 22, 2021

(87) PCT Pub. No.: WO2020/195271
PCT Pub. Date: Oct. 1, 2020

(65) Prior Publication Data
US 2022/0192538 A1    Jun. 23, 2022

(30) Foreign Application Priority Data
Mar. 28, 2019  (JP) .................. 2019-064752

(51) Int. Cl.
*A61B 5/11* (2006.01)
*G06T 7/20* (2017.01)
*G06T 7/70* (2017.01)

(52) U.S. Cl.
CPC ............... *A61B 5/112* (2013.01); *G06T 7/20* (2013.01); *G06T 7/70* (2017.01); *G06T 2207/10028* (2013.01)

(58) Field of Classification Search
None
See application file for complete search history.

(56) References Cited

U.S. PATENT DOCUMENTS

| | | | |
|---|---|---|---|
| 9,597,016 B2* | 3/2017 | Stone | A61B 5/112 |
| 2015/0003687 A1* | 1/2015 | Utsunomiya | G06V 40/25 |
| | | | 382/107 |

(Continued)

FOREIGN PATENT DOCUMENTS

| | | |
|---|---|---|
| CN | 107174255 A | 9/2017 |
| CN | 108348195 A | 7/2018 |

(Continued)

OTHER PUBLICATIONS

International Search Report for PCT Application No. PCT/JP2020/005349, mailed on Apr. 21, 2020.

(Continued)

*Primary Examiner* — Leon Viet Q Nguyen (57) ABSTRACT

A gait analysis apparatus 10 includes, a data acquisition unit 11 that acquires a three-dimensional point cloud data of a human to be analyzed, a center of gravity location calculation unit 12 that calculates coordinates of a center of gravity location on the three-dimensional point cloud data of the human to be analyzed by using coordinates of each point constituting the acquired three-dimensional point cloud data, and a gait index calculation unit 13 that calculates a gait index of the human to be analyzed by using the calculated center of gravity location.

9 Claims, 6 Drawing Sheets

(56) References Cited

U.S. PATENT DOCUMENTS

| | | | |
|---|---|---|---|
| 2018/0325467 A1 | 11/2018 | Matsumura et al. | |
| 2018/0338710 A1* | 11/2018 | Tas | A61B 5/4082 |
| 2019/0108740 A1* | 4/2019 | Coke | G01S 13/726 |

FOREIGN PATENT DOCUMENTS

| | | |
|---|---|---|
| JP | 2007-125368 A | 5/2007 |
| JP | 2017-023689 A | 2/2017 |
| JP | 2018-038753 A | 3/2018 |
| JP | 2018-099267 A | 6/2018 |
| JP | 2019-025134 A | 2/2019 |
| WO | 2017/085914 A1 | 5/2017 |

OTHER PUBLICATIONS

Gerald F. Harris et al., "Procedures for Gait Analysis", Archives of Physical Medicine and Rehabilitation, vol. 75, Issue 2, Feb. 1994, pp. 216-225.

Kotaro Takata et al., "Gait Evaluation With A Small Three-dimensional Accelerometer", Tokyo Jikeikai Medical Journal, vol. 119, issue.5, Sep. 15, 2004, pp. 331-338.

English translation of Written opinion for PCT Application No. PCT/JP2020/005349, mailed on Apr. 21, 2020.

JP Office Action for JP Application No. 2021-508218, mailed on Aug. 23, 2022 with English Translation.

Chinese Office Action for CN Application No. 202080024144.4 mailed on Nov. 20, 2023 with English Translation.

\* cited by examiner

GAIT ANALYSIS APPARATUS, GAIT ANALYSIS METHOD, AND COMPUTER-READABLE RECORDING MEDIUM

This application is a National Stage Entry of PCT/JP2020/005349 filed on Feb. 12, 2020, which claims priority from Japanese Patent Application 2019-064752 filed on Mar. 28, 2019, the contents of all of which are incorporated herein by reference, in their entirety.

TECHNICAL FIELD

The present invention relates to a gait analysis apparatus and a gait analysis method for analyzing a human's gait, and further relates to a computer-readable recording medium on which a program for realizing these is recorded.

BACKGROUND ART

In recent years, a technique for analyzing a human gait has attracted attention. This is because it is considered that the health condition and physical ability of the human can be estimated by analyzing the gait, and the health can be promoted. Therefore, techniques for gait analysis have been proposed (see, for example, Patent Document 1, Non-Patent Documents 1 and 2).

Specifically, Patent Document 1 and Non-Patent Documents 1 and 2 each disclose a system for analyzing the human gait. Of these, the system disclosed in Non-Patent Document 1 analyzes the human gait based on pressure on a floor during walking measured by a floor reaction force meter attached to the floor and coordinates of each joint acquired by a motion capture system. On the other hand, the systems disclosed in Non-Patent Document 2 and Patent Document 1 analyze the human gait based on a sensor signal from an acceleration sensor attached to a waist of a pedestrian.

LIST OF RELATED ART DOCUMENTS

Patent Documents

[Patent Document 1] Japanese Patent Laid-Open Publication No. 2018-38753

Non-Patent Documents

[Non-Patent Document 1] Gerald F. Harris, Jacqueline J. Wertsch, "Procedures for Gait Analysis", Arch. Phys. Med. Rehab., 75 (1994), pp. 216-225
[Non-Patent Document 2] Kotaro Takata, Masahiro Abo, "Gait evaluation with a small three-dimensional accelerometer", Jikei Medical Journal, 2004

SUMMARY OF INVENTION

Problems to be Solved by the Invention

Incidentally, when the system disclosed in Non-Patent Document 1 is adopted, it is necessary to attach a marker to each joint of a human to be analyzed. Further, when the system disclosed in Non-Patent Document 2 or Patent Document 1 is adopted, it is necessary to attach an acceleration sensor to the waist of the human to be analyzed. Therefore, these systems have a problem that the human to be analyzed is burdened. In addition, the subjects of gait analysis are often those with walking disabilities and the elderly, and the burden is required to be as small as possible.

An example object of the present invention is to provide a gait analysis apparatus, a gait analysis method, and a computer-readable recording medium that solve the aforementioned problem and analyzes the gait of the human to be analyzed while suppressing the burden on the human to be analyzed.

Means for Solving the Problems

In order to achieve the above object, a gait analysis apparatus in one aspect of the present invention includes:
  a data acquisition unit that acquires a three-dimensional point cloud data of a human to be analyzed,
  a center of gravity location calculation unit that calculates coordinates of a center of gravity location on the three-dimensional point cloud data of the human to be analyzed by using coordinates of each point constituting the acquired three-dimensional point cloud data, and
  a gait index calculation unit that calculates a gait index of the human to be analyzed by using the calculated center of gravity location.

Further, in order to achieve the above object, a gait analysis method in one aspect of the present invention includes:
  a data acquisition step of acquiring a three-dimensional point cloud data of a human to be analyzed,
  a center of gravity location calculation step of calculating coordinates of a center of gravity location on the three-dimensional point cloud data of the human to be analyzed by using coordinates of each point constituting the acquired three-dimensional point cloud data, and
  a gait index calculation step of calculating a gait index of the human to be analyzed by using the calculated center of gravity location.

Further, in order to achieve the above object, a computer-readable recording medium that includes a program recorded thereon in one aspect of the present invention, the program including instructions that cause a computer to carry out:
  a data acquisition step of acquiring a three-dimensional point cloud data of a human to be analyzed,
  a center of gravity location calculation step of calculating coordinates of a center of gravity location on the three-dimensional point cloud data of the human to be analyzed by using coordinates of each point constituting the acquired three-dimensional point cloud data, and
  a gait index calculation step of calculating a gait index of the human to be analyzed by using the calculated center of gravity location.

Advantageous Effects of the Invention

As described above, according to the present invention, it is possible to analyze the gait of the human to be analyzed while suppressing the burden on the human to be analyzed.

EXAMPLE EMBODIMENTS

Example Embodiment

Hereinafter, a gait analysis apparatus, a gait analysis method and a program according to the example embodiment will be described with reference to FIGS. 1 to 6.

[Apparatus Configuration]

Figure 1:
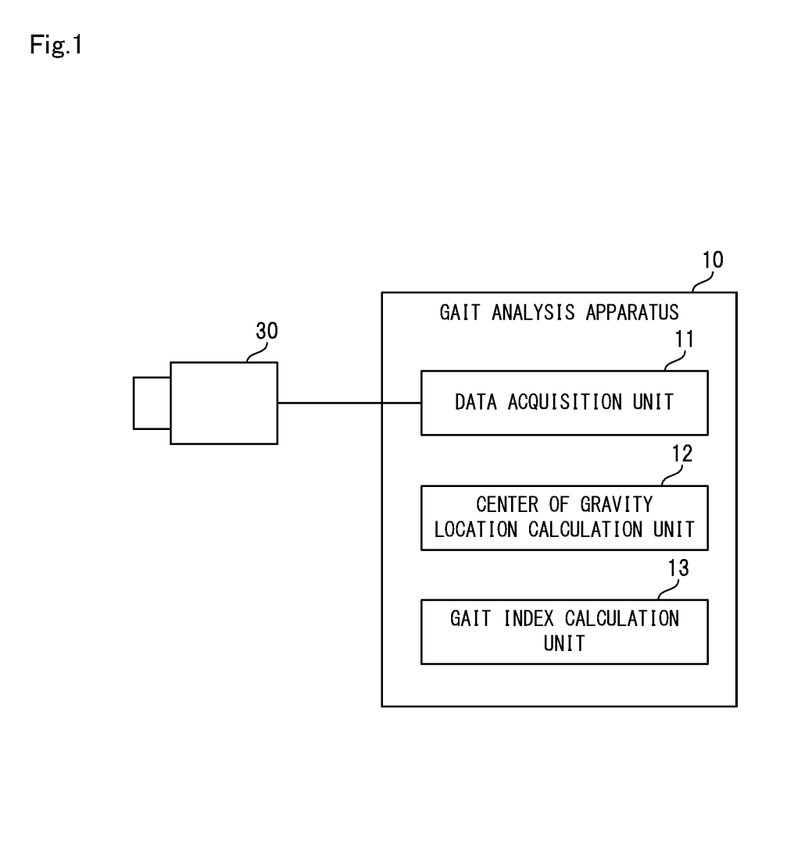
FIG. 1 is a block diagram showing a schematic configuration of a gait analysis apparatus according to an example embodiment.

First, the configuration of a gait analysis apparatus according to the example embodiment will be described with reference to FIG. 1. FIG. 1 is a diagram showing an example of the gait analysis apparatus.

The gait analysis apparatus 10 according to the example embodiment shown in FIG. 1 is an apparatus for analyzing a gait of the human to be analyzed 20. As shown in FIG. 1, the gait analysis apparatus 10 includes a data acquisition unit 11, a center of gravity location calculation unit 12, and a gait index calculation unit 13.

The data acquisition unit 11 acquires a three-dimensional point cloud data of the human to be analyzed 20. The center of gravity location calculation unit 12 calculates coordinates of a center of gravity location on the three-dimensional point cloud data of the human to be analyzed 20 by using coordinates of each point constituting the three-dimensional point cloud data acquired by the data acquisition unit 11. The gait index calculation unit 13 calculates a gait index of the human to be analyzed 20 using the center of gravity location calculated by the center of gravity location calculation unit 12.

As described above, in the example embodiment, the gait index can be calculated using only the three-dimensional point cloud data of the human to be analyzed 20. Further, the three-dimensional point cloud data can be acquired by using a dedicated imaging device without attaching a sensor, a marker, or the like to the human to be analyzed 20. Therefore, according to the example embodiment, it is possible to analyze the gait of the human to be analyzed while suppressing the burden on the human to be analyzed.

Subsequently, in addition to FIG. 1, the configuration and function of the gait analysis apparatus will be specifically described with reference to FIGS. 2 to 4. First, as shown in FIG. 1, in the example embodiment, the gait analysis apparatus 10 is connected to the imaging device 30.

The imaging device 30 is a device capable of measuring a distance to the subject for each pixel. Specific examples of the imaging device 30 include a TOF (Time-of-Flight) camera. The TOF camera irradiates the subject with light such as near-infrared light, and measures time it takes for the irradiated light to be reflected by the subject and returns to the TOF camera. The TOF camera measures the distance to the subject for each pixel based on the measured time and outputs a data for specifying the measured distance for each pixel. In the example embodiment, this output data becomes three-dimensional point cloud data.

Figure 2:
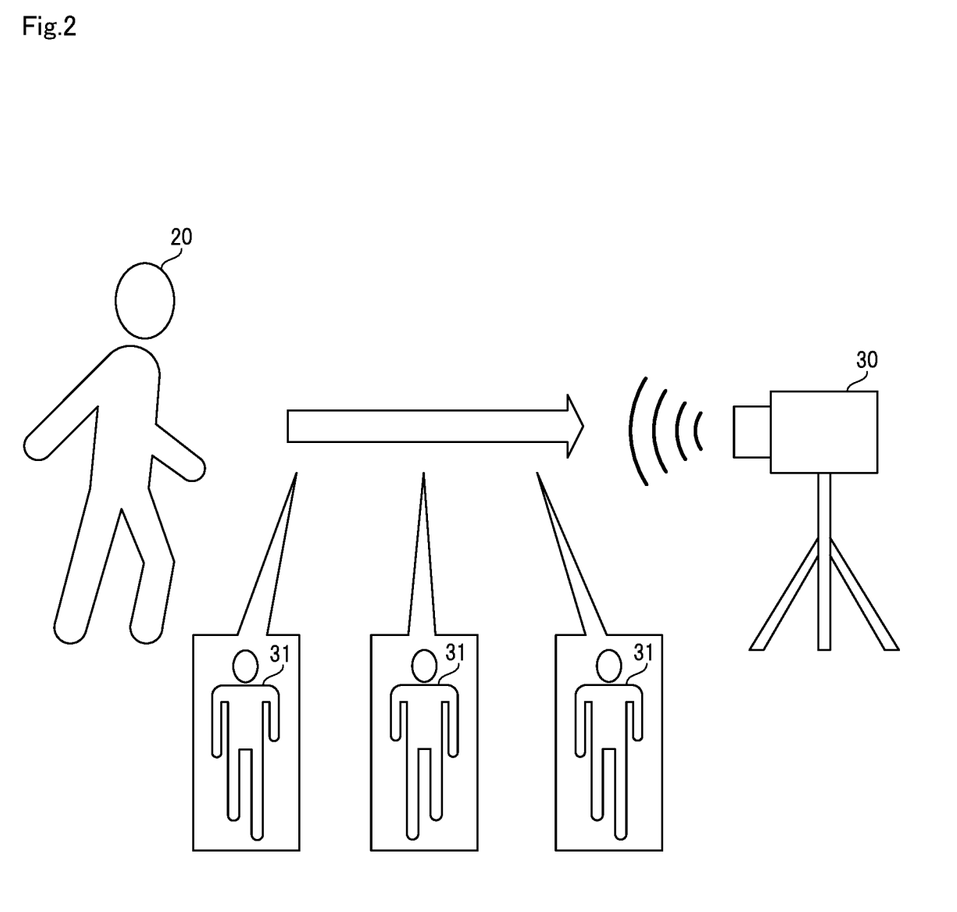
FIG. 2 is a diagram showing a positional relationship between a imaging device used in the example embodiment and the human to be analyzed.

FIG. 2 is a diagram showing a positional relationship between the imaging device used in the example embodiment and the human to be analyzed. FIG. 3 is a diagram showing an example of three-dimensional point cloud data output from the imaging device in the example embodiment. As shown in FIG. 2, in the example embodiment, the imaging device 30 is arranged so that a front of the walking human to be analyzed 20 can be captured. In this case, the imaging device 30 outputs, for example, the three-dimensional point cloud data 31 shown in FIG. 3.

Figure 3:
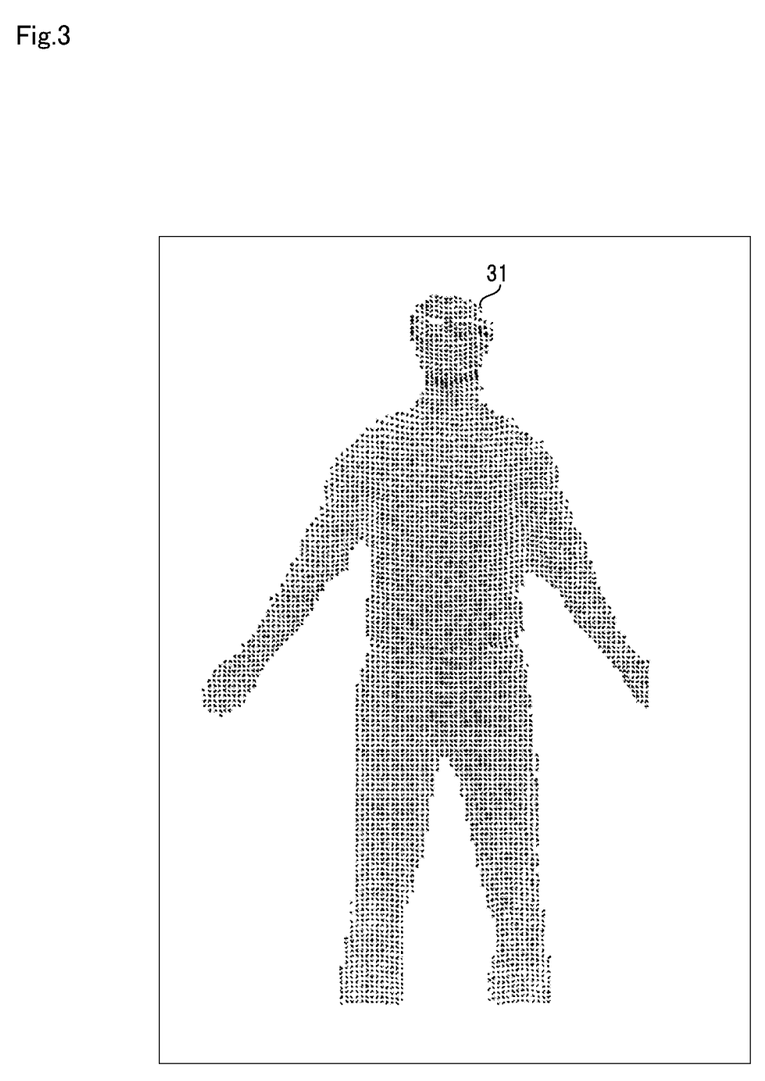
FIG. 3 is a diagram showing an example of three-dimensional point cloud data output from the imaging device in the example embodiment.

As shown in FIG. 3, the three-dimensional point cloud data 31 is acquired by measuring the distance from the imaging device to the subject for each pixel. Therefore, the three-dimensional point cloud data 31 has, for each of the points constituting itself, a coordinate in the horizontal direction (X direction), a coordinate in the vertical direction (Y direction), and a coordinate in depth direction (Z direction) corresponding to the distance.

Further, in the example embodiment, as shown in FIG. 2, the imaging device 30 performs imaging with the human to be analyzed 20 as a subject at set intervals. The imaging device 30 continuously outputs the three-dimensional point cloud data 31 at the set intervals. Therefore, in the example of FIG. 2, when the human to be analyzed 20 walks on a set course so as to approach the imaging device 30, three-dimensional point cloud data 31 showing the gait state along the time series can be acquired. Further, in this case, in the example embodiment, the data acquisition unit 11 acquires the three-dimensional point cloud data 31 for each of the set intervals.

The center of gravity location calculation unit 12, in the example embodiment, calculates the coordinates of the center of gravity location for each of the three-dimensional point cloud data acquired by the data acquisition unit 11 at each of the set intervals. Therefore, in the example of FIG. 2, the coordinates of the position of the center of gravity are calculated along the time series according to the walking of the human to be analyzed 20.

Further, in the example embodiment, the center of gravity location calculation unit 12 calculates a representative value in the horizontal direction from the coordinate in the horizontal direction of each point constituting the three-dimensional point cloud data, and calculates a representative value in the vertical direction from the coordinate in the vertical direction of each point. Also, the center of gravity location calculation unit 12 calculates a representative value in the depth direction from the coordinate in the depth direction of each point. Then, the center of gravity location calculation unit 12 can set the calculated representative values in each direction as the coordinates of the center of gravity location.

The gait index calculation unit 13, in the example embodiment, calculates any or all of a moving speed, a numerical value indicating straightness during movement, and a ground contact timing during walking, of the human to be analyzed 20, as the gait index.

Specifically, the gait index calculation unit 13 obtains a time-series change of the coordinate of the center of gravity location in the depth direction from the coordinates of the center of gravity location calculated for each of the set intervals, and calculates the moving speed of the human to be analyzed 20 as the gait index based on the acquired time-series change.

Further, the gait index calculation unit 13 obtains a time-series change of the coordinate of the center of gravity location in the horizontal direction from the coordinates of the center of gravity location calculated for each of the set intervals, and calculates the a numerical value indicating straightness during moving of the human to be analyzed 20 as the gait index based on the acquired time-series change.

Further, the gait index calculation unit 13 acquires a time-series change of the coordinate of the center of gravity location in the vertical direction from the coordinates of the center of gravity location calculated for each of the set intervals, and calculates the ground contact timing during walking of the human to be analyzed 20 as the gait index based on the acquired time-series change.

Figure 4:
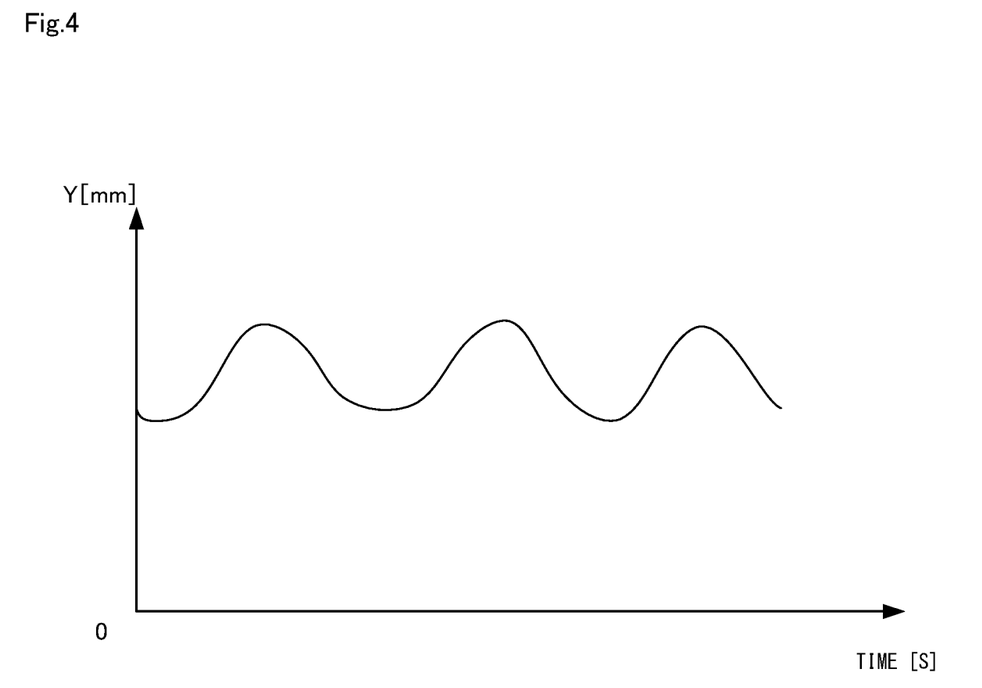
FIG. 4 is a diagram showing an example of time-series changes in a coordinate in the vertical direction of a center of gravity location calculated in the example embodiment.

FIG. 4 is a diagram showing an example of time-series changes in coordinates in the vertical direction of the center of gravity location calculated in the example embodiment. As shown in FIG. 4, the coordinate of the position of the center of gravity in the vertical direction (Y direction) move up and down according to the walking cycle. Therefore, the gait index calculation unit 13 can set, for example, a time when a direction of the coordinate value change turns from negative to positive as the ground contact timing. Further, the gait index calculation unit 13 can also set a time when the coordinate value becomes the lowest point as the ground contact timing.

Further, in those case, the gait index calculation unit 13 may specify a point closest to the ground from each of the three-dimensional point cloud data acquired by the data acquisition unit 11 for each of the set intervals, for each of the calculated ground contact timing. In this case, the gait index calculation unit 13 can determine whether a foot touching the ground at the ground contact timing is right or left based on the coordinates of the specified point in the horizontal direction.

[Apparatus Operations]

Figure 5:
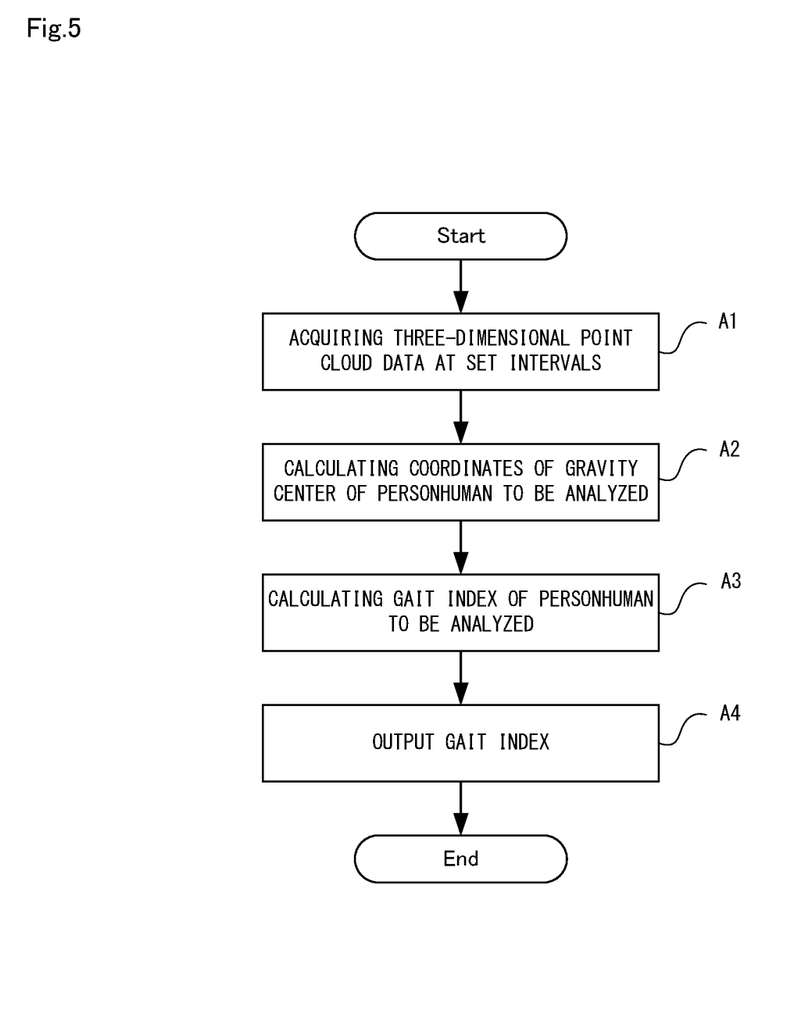
FIG. 5 is a flow diagram showing operation of the gait analysis apparatus according to the example embodiment.

Next, operations of a gait analysis apparatus according to the example embodiment will be described with reference to FIG. 5. FIG. 5 is a flow diagram showing operation of the gait analysis apparatus according to the example embodiment. In the following description, FIGS. 1 to 4 are referenced as appropriate. Also, in this example embodiment, the gait analysis method is implemented by operating the gait analysis apparatus. Therefore, a description of the gait analysis method according to the example embodiment will be replaced with the following description of the operation of the gait analysis apparatus 10.

First, as a premise, as shown in FIG. 2, the human to be analyzed 20 walks on the set course so as to approach the imaging device 30. As a result, the imaging device 30 continuously outputs the three-dimensional point cloud data at set intervals while the human to be analyzed 20 is walking on the course.

As shown in FIG. 5, first, in the gait analysis apparatus 10, the data acquisition unit 11 continuously acquires the three-dimensional point cloud data output from the imaging device 30 at each of the set intervals (step A1). The data acquisition unit 11 outputs the acquired three-dimensional point cloud data for each of the set intervals to the center of gravity location calculation unit 12.

Next, the center of gravity location calculation unit 12 calculates the coordinates of the center of gravity location for each of the three-dimensional point cloud data acquired at each of the set intervals in step A1 (step A2). Specifically, the center of gravity location calculation unit 12 calculates a representative value in the horizontal direction, a representative value in the vertical direction, and a representative value in the depth direction from the three-dimensional point cloud data and sets the calculated representative values in each direction as the coordinates of the center of gravity location.

Next, the gait index calculation unit 13 calculates the gait index of the human to be analyzed using the center of gravity location calculated in step A2 (step A3). Specifically, the gait index calculation unit 13 calculates, as the gait index, any or all of the moving speed, the numerical value indicating the straightness during movement, and the ground contact timing during walking, of the human to be analyzed 20.

Subsequently, the gait index calculation unit 13 outputs the calculated gait index to an external display device, a terminal device, or the like (step A4). As a result, the gait index is displayed on a screen of the display device, the terminal device, or the like, and the analyst can give a health advice to the human to be analyzed 20.

[Effects of Example Embodiment]

As described above, according to the example embodiment, the human to be analyzed 20 can be analyzed by simply capture the walking of the human to be analyzed 20 by the imaging device 30 capable of outputting the three-dimensional point cloud data. In addition, the gait index can be acquired as the analysis result. That is, according to the example embodiment, it is possible to analyze the gait of the human to be analyzed while suppressing the burden on the human to be analyzed.

[Program]

It suffices for the program according to the example embodiment to be a program that causes a computer to execute steps A1 to A4 shown in FIG. 5. The gait analysis apparatus and the gait analysis method according to the example embodiment can be realized by installing the program in a computer and executing the program. In this case, a processor of the computer functions as the data acquisition unit 11, the center of gravity location calculation unit 12, and the gait index calculation unit 13, and performs the processing.

The program according to the example embodiment may be executed by a computer system constructed from a plurality of computers. In this case, for example, each computer may function as one of the data acquisition unit 11, the center of gravity location calculation unit 12, and the gait index calculation unit 13.

Figure 6:
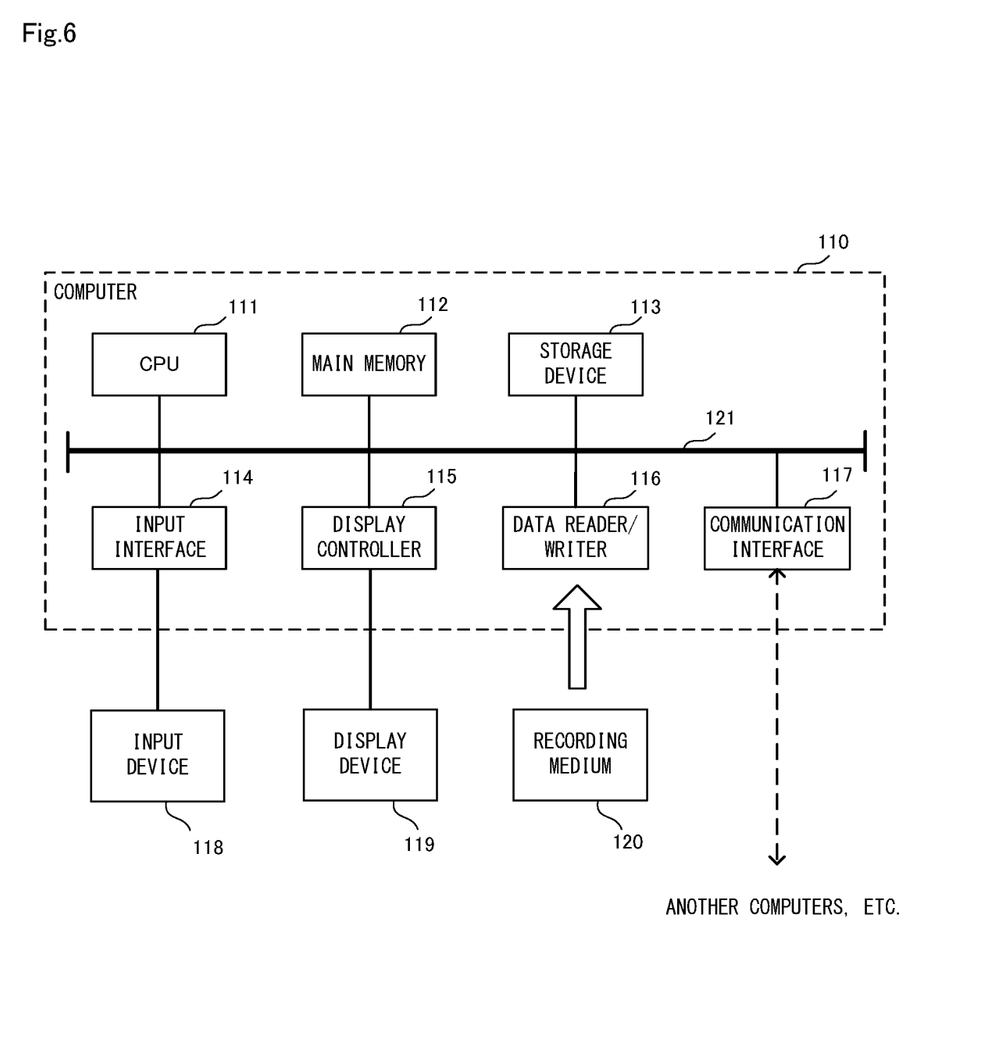
FIG. 6 is a block diagram showing an example of a computer that realizes the gait analysis apparatus according to the example embodiment.

Here, a computer that realizes the gait analysis apparatus 10 by executing the program of the example embodiments will be described using FIG. 6. FIG. 6 is a block diagram showing an example of the computer that realizes the gait analysis apparatus according to the example embodiment.

As shown in FIG. 6, a computer 110 includes a CPU (Central Processing Unit) 111, a main memory 112, a storage device 113, an input interface 114, a display controller 115, a data reader/writer 116, and a communication interface 117. These components are connected to in such a manner that they can perform data communication with one another via a bus 121. Note that the computer 110 may include a GPU (Graphics Processing Unit) or an FPGA (Field-Programmable Gate Array), in addition to the CPU 111 or instead of the CPU 111.

The CPU 111 implements various computational operations, by developing the program (codes) according to the example embodiment stored in the storage device 113 to the main memory 112, and executing the codes in a predetermined order. The main memory 112 is typically a volatile storage device such as a DRAM (Dynamic Random-Access Memory). Also, the program in the example embodiment are provided in a state of being stored in a computer-readable recording medium 120. Note that the program according to the example embodiment may be distributed over the Internet connected via the communication interface 117.

Also, specific examples of the storage device 113 include a hard disk drive and a semiconductor storage device, such as a flash memory. The input interface 114 mediates data transmission between the CPU 111 and input device 118 such as a keyboard and a mouse. The display controller 115 is connected to a display device 119 and controls display on the display device 119.

The data reader/writer 116 mediates data transmission between the CPU 111 and the recording medium 120, read out the program from the recording medium 120 and writes the results of processing in the computer 110 to the recording medium 120. The communication interface 117 mediates data transmission between the CPU 111 and another computers.

Also, specific examples of the recording medium 1200 include: a general-purpose semiconductor storage device, such as CF (CompactFlash®) and SD (Secure Digital); a magnetic recording medium, such as a flexible disk; and an optical recording medium, such as a CD-ROM (Compact Disk Read Only Memory).

Note that the gait analysis apparatus 10 in the example embodiment can be realizable by using item of hardware that respectively corresponds to the components, rather than the computer in which the program is installed. Furthermore, a part of the gait analysis apparatus 10 may be realized by the program, and the remaining portion part of the gait analysis apparatus 10 may be realized by hardware.

A part or an entirety of the above-described example embodiment can be represented by (Supplementary Note 1) to (Supplementary Note 18) described below, but is not limited to the description below.

Supplementary Note 1

A gait analysis apparatus including,
a data acquisition unit configured to acquire a three-dimensional point cloud data of a human to be analyzed,
a center of gravity location calculation unit configured to calculate coordinates of a center of gravity location on the three-dimensional point cloud data of the human to be analyzed by using coordinates of each point constituting the acquired three-dimensional point cloud data, and
a gait index calculation unit configured to calculate a gait index of the human to be analyzed by using the calculated center of gravity location.

Supplementary Note 2

The gait analysis apparatus according to Supplementary note 1, wherein
the three-dimensional point cloud data is acquired by an imaging device which can measure a distance to a subject for each pixel, and the three-dimensional point has, for each of points constituting itself, a coordinate in the horizontal direction, a coordinate in the vertical direction, and a coordinate in depth direction corresponding to the distance, and
the center of gravity location calculation unit calculates a representative value in the horizontal direction from the coordinate in the horizontal direction of the each point, a representative value in the vertical direction from the coordinate in the vertical direction of the each point, and a representative value in the depth direction from the coordinate in the depth direction of the each point, and set the calculated representative values in each direction as the coordinates of the center of gravity location.

Supplementary Note 3

The gait analysis apparatus according to Supplementary note 2, wherein
when the imaging device performs imaging with the human to be analyzed as a subject at set intervals, the data acquisition unit acquires the three-dimensional point cloud data of each of the set intervals,
the center of gravity location calculation unit calculates the coordinates of the center of gravity location at each of the set intervals from each of the acquired three-dimensional point cloud data,
the gait index calculation unit obtains a time-series change of the coordinate of the center of gravity location in the depth direction from the coordinates of the center of gravity location calculated for each of the set intervals and calculates a moving speed of the human to be analyzed as the gait index based on the obtained time-series change.

Supplementary Note 4

The gait analysis apparatus according to Supplementary note 2, wherein
when the imaging device performs imaging with the human to be analyzed as a subject at set intervals, the data acquisition unit acquires the three-dimensional point cloud data of each of the set intervals,
the center of gravity location calculation unit calculates the coordinates of the center of gravity location at each of the set intervals from each of the acquired three-dimensional point cloud data,
the gait index calculation unit obtains a time-series change of the coordinate of the center of gravity location in the horizontal direction from the coordinates of the center of gravity location calculated for each of the set intervals and calculates a numerical value indicating straightness during moving of the human to be analyzed as the gait index based on the obtained time-series change.

Supplementary Note 5

The gait analysis apparatus according to Supplementary note 2, wherein
when the imaging device performs imaging with the human to be analyzed as a subject at set intervals, the data acquisition unit acquires the three-dimensional point cloud data of each of the set intervals,
the center of gravity location calculation unit calculates the coordinates of the center of gravity location at each of the set intervals from each of the acquired three-dimensional point cloud data,
the gait index calculation unit obtains a time-series change of the coordinate of the center of gravity location in the vertical direction from the coordinates of the center of gravity location calculated for each of the set intervals and calculates a ground contact timing during walking of the human to be analyzed as the gait index based on the obtained time-series change.

Supplementary Note 6

The gait analysis apparatus according to Supplementary note 5, wherein
  the gait index calculation unit specifies a point closest to the ground from each of the acquired three-dimensional point cloud data for each of the set intervals and determines whether a foot touching the ground at the ground contact timing is right or left based on the coordinate of the specified point in the horizontal direction.

Supplementary Note 7

A gait analysis method including,
a data acquisition step acquiring a three-dimensional point cloud data of a human to be analyzed,
a center of gravity location calculation step calculating coordinates of a center of gravity location on the three-dimensional point cloud data of the human to be analyzed by using coordinates of each point constituting the acquired three-dimensional point cloud data, and
a gait index calculation step calculating a gait index of the human to be analyzed by using the calculated center of gravity location.

Supplementary Note 8

The gait analysis method according to Supplementary note 7, wherein
  the three-dimensional point cloud data is acquired by an imaging device which can measure a distance to a subject for each pixel, and the three-dimensional point has, for each of points constituting itself, a coordinate in the horizontal direction, a coordinate in the vertical direction, and a coordinate in depth direction corresponding to the distance, and
  in the center of gravity location calculation step, a representative value in the horizontal direction is calculated from the coordinate in the horizontal direction of the each point, a representative value in the vertical direction is calculated from the coordinate in the vertical direction of the each point, and a representative value in the depth direction is calculated from the coordinate in the depth direction of the each point, and the calculated representative values in each direction are set as the coordinates of the center of gravity location.

Supplementary Note 9

The gait analysis method according to Supplementary note 8, wherein
  when the imaging device performs imaging with the human to be analyzed as a subject at set intervals, the three-dimensional point cloud data of each of the set intervals is acquired,
  in the center of gravity location calculation step, the coordinates of the center of gravity location at each of the set intervals is calculated from each of the acquired three-dimensional point cloud data,
  in the gait index calculation step, a time-series change of the coordinate of the center of gravity location in the depth direction is obtained from the coordinates of the center of gravity location calculated for each of the set intervals, and a moving speed of the human to be analyzed is calculated as the gait index based on the obtained time-series change.

Supplementary Note 10

The gait analysis method according to Supplementary note 8, wherein
  when the imaging device performs imaging with the human to be analyzed as a subject at set intervals, in the data acquisition step, the three-dimensional point cloud data of each of the set intervals is acquired,
  in the center of gravity location calculation step, the coordinates of the center of gravity location at each of the set intervals is calculated from each of the acquired three-dimensional point cloud data,
  in the gait index calculation step, a time-series change of the coordinate of the center of gravity location in the horizontal direction is obtained from the coordinates of the center of gravity location calculated for each of the set intervals, and a numerical value indicating straightness during moving of the human to be analyzed is calculated as the gait index based on the obtained time-series change.

Supplementary Note 11

The gait analysis method according to Supplementary note 8, wherein
  when the imaging device performs imaging with the human to be analyzed as a subject at set intervals, the three-dimensional point cloud data of each of the set intervals is acquired,
  in the center of gravity location calculation step, the coordinates of the center of gravity location at each of the set intervals is calculated from each of the acquired three-dimensional point cloud data,
  in the gait index calculation step, a time-series change of the coordinates of the center of gravity location in the vertical direction is obtained from the coordinates of the center of gravity location calculated for each of the set intervals, and a ground contact timing during walking of the human to be analyzed is calculated as the gait index based on the obtained time-series change.

Supplementary Note 12

The gait analysis method according to Supplementary note 11, wherein
  in the gait index calculation step, a point closest to the ground is specified from each of the acquired three-dimensional point cloud data for each of the set intervals, and
  whether a foot touching the ground at the ground contact timing is right or left is determined based on the coordinate of the specified point in the horizontal direction.

Supplementary Note 13

A computer-readable recording medium that includes a program recorded thereon, the program including instructions that cause a computer to carry out,
  acquiring a three-dimensional point cloud data of a human to be analyzed,
  calculating coordinates of a center of gravity location on the three-dimensional point cloud data of the human to be analyzed by using coordinates of each point constituting the acquired three-dimensional point cloud data, and calculating a gait index of the human to be analyzed by using the calculated center of gravity location.

Supplementary Note 14

The computer-readable recording medium according to Supplementary note 13, wherein
the three-dimensional point cloud data is acquired by an imaging device which can measure a distance to a subject for each pixel, and the three-dimensional point has, for each of points constituting itself, a coordinate in the horizontal direction, a coordinate in the vertical direction, and a coordinate in depth direction corresponding to the distance, and
in the center of gravity location calculation step, a representative value in the horizontal direction is calculated from the coordinate in the horizontal direction of the each point, a representative value in the vertical direction is calculated from the coordinate in the vertical direction of the each point, and a representative value in the depth direction is calculated from the coordinate in the depth direction of the each point, and the calculated representative values in each direction are set as the coordinates of the center of gravity location.

Supplementary Note 15

The computer-readable recording medium according to Supplementary note 14, wherein
when the imaging device performs imaging with the human to be analyzed as a subject at set intervals, in the data acquisition step, the three-dimensional point cloud data of each of the set intervals is acquired,
in the center of gravity location calculation step, the coordinates of the center of gravity location at each of the set intervals is calculated from each of the acquired three-dimensional point cloud data,
in the gait index calculation step, a time-series change of the coordinate of the center of gravity location in the depth direction is obtained from the coordinates of the center of gravity location calculated for each of the set intervals, and a moving speed of the human to be analyzed is calculated as the gait index based on the obtained time-series change.

Supplementary Note 16

The computer-readable recording medium according to Supplementary note 14, wherein
when the imaging device performs imaging with the human to be analyzed as a subject at set intervals, in the data acquisition step, the three-dimensional point cloud data of each of the set intervals is acquired,
in the center of gravity location calculation step, the coordinates of the center of gravity location at each of the set intervals is calculated from each of the acquired three-dimensional point cloud data,
in the gait index calculation step, a time-series change of the coordinate of the center of gravity location in the horizontal direction is obtained from the coordinates of the center of gravity location calculated for each of the set intervals, and a numerical value indicating straightness during moving of the human to be analyzed is calculated as the gait index based on the obtained time-series change.

Supplementary Note 17

The computer-readable recording medium according to Supplementary note 14, wherein
when the imaging device performs imaging with the human to be analyzed as a subject at set intervals, in the data acquisition step, the three-dimensional point cloud data of each of the set intervals is acquired,
in the center of gravity location calculation step, the coordinates of the center of gravity location at each of the set intervals is calculated from each of the acquired three-dimensional point cloud data,
in the gait index calculation step, a time-series change of the coordinates of the center of gravity location in the vertical direction is obtained from the coordinates of the center of gravity location calculated for each of the set intervals, and a ground contact timing during walking of the human to be analyzed is calculated as the gait index based on the obtained time-series change.

Supplementary Note 18

The computer-readable recording medium according to Supplementary note 17, wherein
in the gait index calculation step, a point closest to the ground is specified from each of the acquired three-dimensional point cloud data for each of the set intervals, and
whether a foot touching the ground at the ground contact timing is right or left is determined based on the coordinate of the specified point in the horizontal direction.

Although the present invention has been described above with reference to the example embodiments, the present invention is not limited to the above example embodiments. The configuration and details of the present invention can be made various changes that can be understood by those skilled in the art within the scope of the present invention.

This application claims priority from Japanese Patent Application No. 2019-064752, filed Mar. 28, 2019, and the entire content thereof is hereby incorporated by reference herein.

INDUSTRIAL APPLICABILITY

As described above, according to the present invention, it is possible to analyze the gait of the human to be analyzed while suppressing the burden on the human to be analyzed. The present invention is useful in various fields where gait analysis is required.

REFERENCE SIGNS LIST 10 gait analysis apparatus
11 data acquisition unit
12 center of gravity location calculation unit
13 gait index calculation unit
20 human to be analyzed
30 imaging device
110 computer
111 CPU
112 main memory
113 storage device
114 input interface 115 display controller
116 data reader/writer
117 communication interface
118 input device
119 display device
120 recording medium
121 bus

The invention claimed is:

1. A gait analysis apparatus comprising:
a memory storing instructions; and
a processor is configured to execute the instructions to:
acquire a three-dimensional point cloud data of a human to be analyzed, the three-dimensional point cloud data acquired by an imaging device that measures a distance to a subject for each of a plurality of pixels, where each point has a coordinate in a horizontal direction, a coordinate in a vertical direction, and a coordinate in a depth direction corresponding to the distance;
calculate coordinates of a center of gravity location on the three-dimensional point cloud data of the human to be analyzed by using coordinates of each point of a plurality of points constituting the acquired three-dimensional point cloud data, by calculating a representative value in the horizontal direction from the coordinate in the horizontal direction of each point, a representative value in the vertical direction from the coordinate in the vertical direction of each point, and a representative value in the depth direction from the coordinate in the depth direction of each point, and set the calculated representative values in each direction as the coordinates of the center of gravity location; and
calculate a gait index of the human to be analyzed by using the calculated center of gravity location, wherein
when the imaging device performs imaging of the human to be analyzed as a subject at set intervals, the processor acquires the three-dimensional point cloud data of each of the set intervals,
the processor calculates the coordinates of the center of gravity location at each of the set intervals from the three-dimensional point cloud data acquired at the each of the set intervals,
the processor obtains a time-series change of the coordinate of the center of gravity location in the vertical direction from the coordinates of the center of gravity location calculated for each of the set intervals and calculates a ground contact timing during walking of the human to be analyzed as the gait index based on the obtained time-series change, and
the processor determines a point closest to the ground from the three-dimensional point cloud data acquired for each of the set intervals, and determines whether a foot touching ground at the ground contact timing is a right foot or a left foot based on the coordinate of the determined point in the horizontal direction.

2. The gait analysis apparatus according to claim 1, wherein
the processor obtains a time-series change of the coordinate of the center of gravity location in the depth direction from the coordinates of the center of gravity location calculated for each of the set intervals and calculates a moving speed of the human to be analyzed as the gait index based on the obtained time-series change.

3. The gait analysis apparatus according to claim 1, wherein
the processor a time-series change of the coordinate of the center of gravity location in the horizontal direction from the coordinates of the center of gravity location calculated for each of the set intervals and calculates a numerical value indicating straightness during moving of the human to be analyzed as the gait index based on the obtained time-series change.

4. A gait analysis method perform by a processor and comprising:
acquiring acquire a three-dimensional point cloud data of a human to be analyzed, the three-dimensional point cloud data acquired by an imaging device that measures a distance to a subject for each of a plurality of pixels, where each point has a coordinate in a horizontal direction, a coordinate in a vertical direction, and a coordinate in a depth direction corresponding to the distance;
calculating coordinates of a center of gravity location on the three-dimensional point cloud data of the human to be analyzed by using coordinates of each point of a plurality of points constituting the acquired three-dimensional point cloud data, by calculating a representative value in the horizontal direction from the coordinate in the horizontal direction of each point, a representative value in the vertical direction from the coordinate in the vertical direction of each point, and a representative value in the depth direction from the coordinate in the depth direction of each point, and set the calculated representative values in each direction as the coordinates of the center of gravity location; and
calculating a gait index of the human to be analyzed by using the calculated center of gravity location, wherein
when the imaging device performs imaging of the human to be analyzed as a subject at set intervals, the processor acquires the three-dimensional point cloud data of each of the set intervals,
the processor calculates the coordinates of the center of gravity location at each of the set intervals from the three-dimensional point cloud data acquired at the each of the set intervals,
the processor obtains a time-series change of the coordinate of the center of gravity location in the vertical direction from the coordinates of the center of gravity location calculated for each of the set intervals and calculates a ground contact timing during walking of the human to be analyzed as the gait index based on the obtained time-series change, and
the processor determines a point closest to the ground from the three-dimensional point cloud data acquired for each of the set intervals, and determines whether a foot touching ground at the ground contact timing is a right foot or a left foot based on the coordinate of the determined point in the horizontal direction.

5. The gait analysis method according to claim 4, wherein
a time-series change of the coordinate of the center of gravity location in the depth direction is obtained from the coordinates of the center of gravity location calculated for each of the set intervals, and a moving speed of the human to be analyzed is calculated as the gait index based on the obtained time-series change.

6. The gait analysis method according to claim 4, wherein
a time-series change of the coordinate of the center of gravity location in the horizontal direction is obtained from the coordinates of the center of gravity location calculated for each of the set intervals, and a numerical value indicating straightness during moving of the human to be analyzed is calculated as the gait index based on the obtained time-series change.

7. A non-transitory computer-readable recording medium storing a program executable by a processor to perform processing comprising:
- acquiring acquire a three-dimensional point cloud data of a human to be analyzed, the three-dimensional point cloud data acquired by an imaging device that measures a distance to a subject for each of a plurality of pixels, where each point has a coordinate in a horizontal direction, a coordinate in a vertical direction, and a coordinate in a depth direction corresponding to the distance;
- calculating coordinates of a center of gravity location on the three-dimensional point cloud data of the human to be analyzed by using coordinates of each point of a plurality of points constituting the acquired three-dimensional point cloud data, by calculating a representative value in the horizontal direction from the coordinate in the horizontal direction of each point, a representative value in the vertical direction from the coordinate in the vertical direction of each point, and a representative value in the depth direction from the coordinate in the depth direction of each point, and set the calculated representative values in each direction as the coordinates of the center of gravity location; and
- calculating a gait index of the human to be analyzed by using the calculated center of gravity location, wherein
- when the imaging device performs imaging of the human to be analyzed as a subject at set intervals, the processor acquires the three-dimensional point cloud data of each of the set intervals,
- the processor calculates the coordinates of the center of gravity location at each of the set intervals from the three-dimensional point cloud data acquired at the each of the set intervals,
- the processor obtains a time-series change of the coordinate of the center of gravity location in the vertical direction from the coordinates of the center of gravity location calculated for each of the set intervals and calculates a ground contact timing during walking of the human to be analyzed as the gait index based on the obtained time-series change, and
- the processor determines a point closest to the ground from the three-dimensional point cloud data acquired for each of the set intervals, and determines whether a foot touching ground at the ground contact timing is a right foot or a left foot based on the coordinate of the determined point in the horizontal direction.

8. The non-transitory computer-readable recording medium according to claim 7, wherein
- a time-series change of the coordinate of the center of gravity location in the depth direction is obtained from the coordinates of the center of gravity location calculated for each of the set intervals, and a moving speed of the human to be analyzed is calculated as the gait index based on the obtained time-series change.

9. The non-transitory computer-readable recording medium according to claim 7, wherein
- a time-series change of the coordinate of the center of gravity location in the horizontal direction is obtained from the coordinates of the center of gravity location calculated for each of the set intervals, and a numerical value indicating straightness during moving of the human to be analyzed is calculated as the gait index based on the obtained time-series change.

* * * * *